United States Patent
Abdelmessih

[11] Patent Number: 6,076,526
[45] Date of Patent: Jun. 20, 2000

[54] MOUTH BREATHING PREVENTER

[76] Inventor: Samy Abdelmessih, 25 Allison Ct., Monmouth Junction, N.J. 08852

[21] Appl. No.: 09/320,302

[22] Filed: May 26, 1999

[51] Int. Cl.[7] .......................................................... A61F 5/56
[52] U.S. Cl. ............................................ 128/848; 128/859
[58] Field of Search ......................... 128/846, 848, 128/859–862; 602/902

[56] References Cited

U.S. PATENT DOCUMENTS

| | | |
|---|---|---|
| 1,354,652 | 10/1920 | Jefferies . |
| 1,629,892 | 5/1927 | Storms . |
| 1,635,272 | 7/1927 | Hartl ........................................ 128/848 |
| 2,882,893 | 4/1959 | Godfroy ................................... 128/848 |
| 4,304,227 | 12/1981 | Samelson . |
| 4,817,636 | 4/1989 | Woods . |
| 5,085,584 | 2/1992 | Boyd . |
| 5,117,816 | 6/1992 | Shapiro ..................................... 128/848 |
| 5,154,184 | 10/1992 | Alvarez ..................................... 128/848 |
| 5,640,974 | 6/1997 | Miller . |
| 5,690,121 | 11/1997 | Miller . |
| 5,720,302 | 2/1998 | Belfer . |

*Primary Examiner*—Michael A. Brown
*Attorney, Agent, or Firm*—Bierman, Muserlian and Lucas

[57] ABSTRACT

The mouth breathing preventer device has a lip shield and a dental shield which are connected by a center tube. The center tube can be sealed to prevent air from entering the mouth or opened to allow for a saline solution or saliva substitute solution to be introduced into the mouth. The device prevents the mouth from dehydrating thereby restoring the self cleansing mechanism of the mouth. The device also helps prevent upper respiratory tract infection, snoring and lessens sinus irritation and middle ear infection.

4 Claims, 5 Drawing Sheets

MOUTH BREATHING PREVENTER

BACKGROUND OF THE INVENTION

1. Field of the Invention

This Invention relates to oral hygiene and, more specifically, to a device that prevents dehydration of the mouth. The Invention is especially intended to be worn by a human while sleeping and, essentially, seals the mouth to force a user to breathe through his nose, not his mouth. The Invention can also be used to prevent snoring, upper respiratory tract infection and to lessen sinus irritation and middle ear infection.

2. Description of the Prior Art

A number of devices have been suggested for sealing the mouth to prevent breathing through the mouth during sleep. Such devices are typically employed to prevent snoring. For example, U.S. Pat. No. 1,629,892 seals the exterior of the mouth with a mouth piece that is held in place with straps that fasten around and behind the head. U.S. Pat. Nos. 1,354,652; 4,817,636; 5,640,974; and 5,690,121 teach mouth pieces of different designs which seal in whole or in part the exterior of the mouth. These mouth pieces employ adhesives to fix the mouth piece to the users face and to maintain the mouth piece in position.

Other devices which have been suggested for preventing snoring are taught in U.S. Pat. Nos. 4,304,227 and 5,720,302. These patents teach mouth pieces which are inserted into the mouth and have a lip shield that covers the exterior of the mouth. The mouthpiece in the '227 patent also has a central socket for the tongue and four channels, two for the teeth and two for the lips. It is molded as an integral unit and completely seals the mouth and separates the jaws and the lips from each other. A problem with such a device is that it raises the bit and may lead to TMJ problems. Furthermore, it prevents swallowing because the tongue is held in the central socket.

The '302 patent teaches a device with one or more holes in the lip shield for breathing and a denture member for covering only the lower teeth and separating the teeth in the lower jaw from the teeth in the upper jaw. The fact that the device of the '302 patent separates the teeth may lead to TMJ problems and will prevent swallowing. Normally, the teeth must be together to allow for swallowing. Furthermore, because of the holes in the lip shield, air can circulate into the mouth leading to dehydration of the mouth.

A device worn in the mouth, over an extended period of time and, especially at night while one is sleeping, should not separate the teeth because separating the teeth, for extended periods of time, can lead to TMJ problems and prevents the normal reflex of swallowing saliva. Furthermore, it is important to promote the flow of saliva in the mouth and to prevent dehydration of the mouth. When the mouth is closed, saliva washes the teeth and prevents bacterial growth around the gingiva and teeth, however, when the mouth is open, the patient automatically breathes through his mouth, causing dehydration of the mouth which, in turn, can lead to bacterial growth and infection. Additionally, it is beneficial in certain circumstances, to employ a saline solution or a saliva substitute solution to wash the teeth and the gum area to assist the saliva in its function.

SUMMARY OF THE INVENTION

Applicant has now discovered a device which prevents mouth breathing and thereby preventing dehydration of the mouth. The device of the Invention also avoids any interference with the teeth occlusion, i.e. allows the teeth to articulate, thereby avoiding lateral or vertical drift of teeth which may lead to TMJ problems. The teeth in the upper and lower jaws can occuled or articulate during swallowing and the lips can take on their normal rest position. The device of the Invention, also allows for a saline solution or other saliva substitute solutions to be introduced into the mouth.

Furthermore, the device of the Invention does not interfere with normal movement of the teeth or jaw or the function of saliva by not covering the saliva ducts orifice or opening. The teeth can move freely allowing a user to cough or vomit as necessary without interference. The device of the Invention allows for swallowing of saliva and does not interfere with the secretion of saliva in the mouth, rather it assists the saliva by preventing air entering the mouth leading to dehydration.

Additionally, by promoting breathing through the nose, it helps to prevent upper respiratory tract infection, snoring and lessens sinus problems which occur due to the lack of nose breathing such as sinus irritation and middle ear infection.

Mouth breathing could be caused by shortening of the upper lip due to thumb sucking, tongue thrust, lower lip biting, etc. The device of the Invention prevents mouth breathing and promotes nose breathing.

Broadly, the device of the Invention comprises:

a lip shield made of molded plastic material shaped to conform to the curvature of both upper and lower lips, said shield extending vertically over both lips and laterally across the complete width of a mouth opening when said mouth is in a rest position, a dental shield made of molded plastic material shaped to conform to the curvature of both upper and lower teeth, said dental shield extending vertically over the teeth in both jaws and laterally across the teeth in both jaws to the second premolar when said mouth is in said rest position; and a center tube connecting said dental shield to said lip shield, said center tube having a hole therein, said center tube adapted to accept a drip tube, and said hole being closable to prevent mouth breathing therethrough.

The three components of the Invention, lip shield, dental shield and center tube, can be molded as one single unit, formed as separate individual pieces which are later joined together, or two of the components can be molded together and later joined to the third component. The joining of the pieces can be either releasable or permanent. Preferably, the three pieces are separately formed and then the center tube is permanently affixed to the dental shield while the lip shield is movably affixed to said center tube.

The device of the Invention can further comprise a retention means for securing the device of the Invention to the user. This retention means insures the proper positioning of the device while the user is asleep or during periods of extended wear. Examples of retention means as taught in the present Invention include, head straps, nose overlays and clasp wires.

Preferably, the lip shield is molded to conform to the lips of the user. Also, preferably, the dental shield is molded to form to the teeth of the user. By molding either one or both of the shields to the users anatomy, a more secure fit is obtained.

BRIEF DESCRIPTION OF THE DRAWINGS

These and other aspects of the present Invention may be more fully understood by reference to one or more of the following drawings.

DETAILED DESCRIPTION OF A PREFERRED EMBODIMENT

The rest position of a users mouth, also referred to as the relaxed position, varies from user to user. However, in the rest position, the users teeth are normally separated by about 1 to 3 mm and the users lips are closed.

The terms vertically and laterally are used to refer to the shields. These terms are used for direction and are oriented with respect to the users head when the user is in an upright, vertical position.

Figure 1:
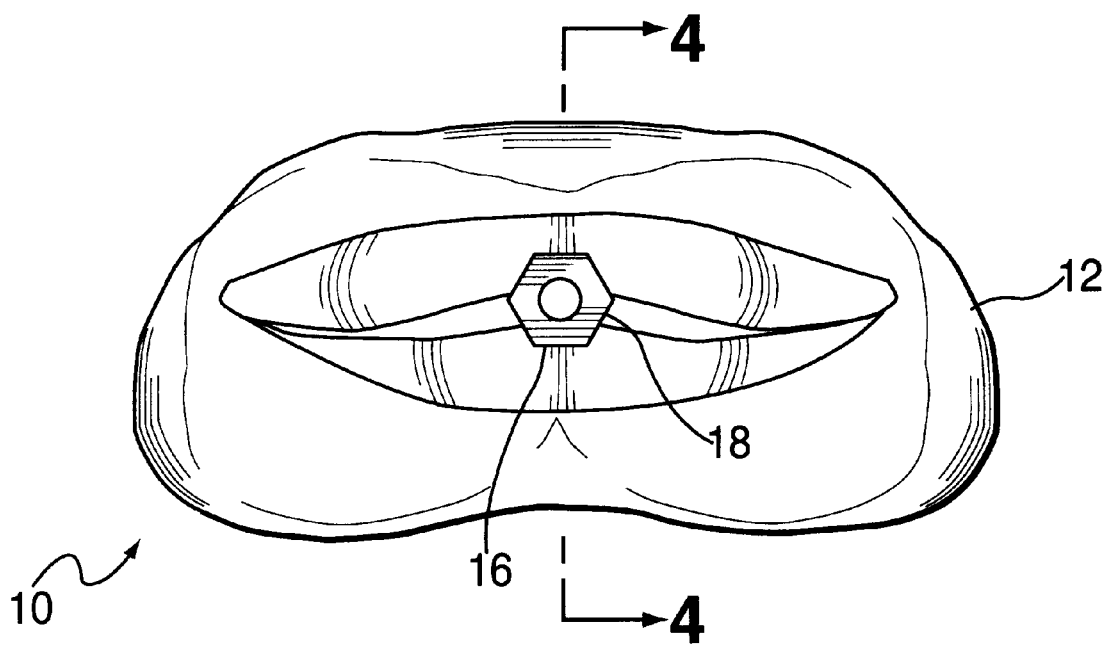
FIG. 1 illustrates a frontal view of a preferred embodiment of the present Invention.
Figure 2:
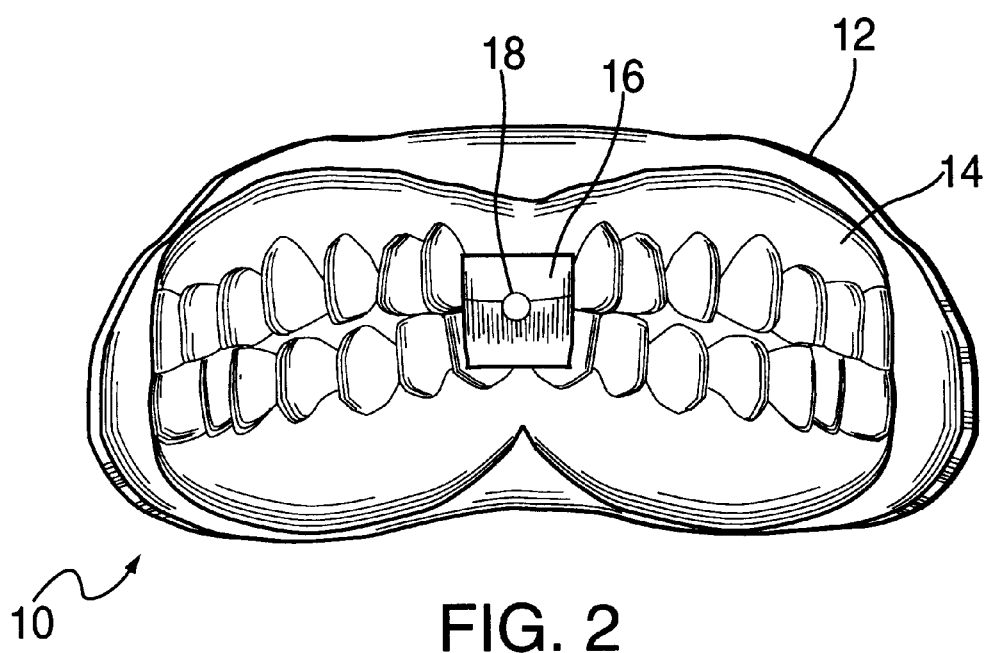
FIG. 2 illustrates a back view of the embodiment of FIG. 1.
Figure 3:
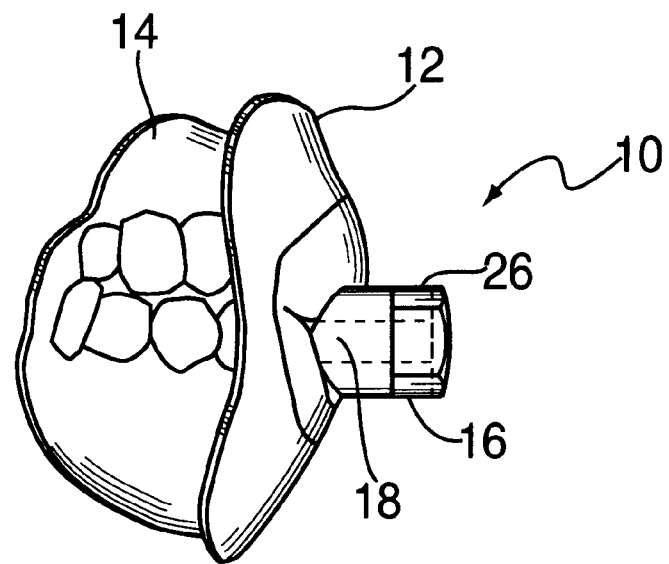
FIG. 3 illustrates a side view of the embodiment of FIG. 1.

Referring now to FIGS. 1, 2, and 3 mouth breathing preventer device 10, is formed from lip shield 12, dental shield 14 and center tube 16. Center tube 16 has hole 18 therethrough to facilitate the drip tube.

Figure 4:
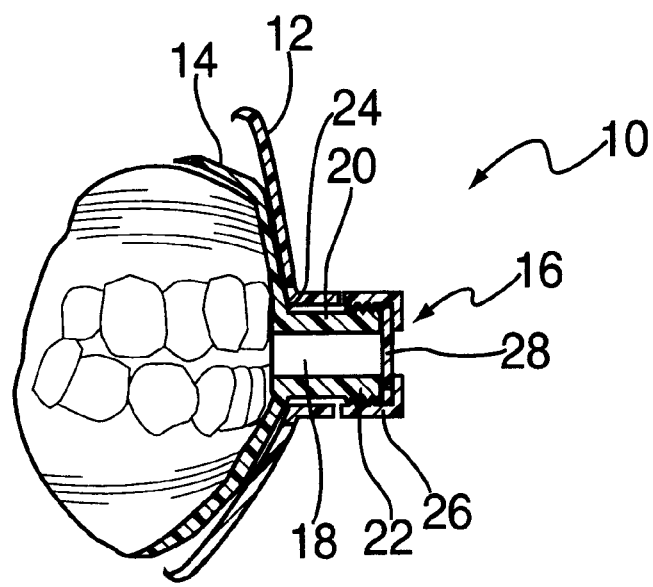
FIG. 4 illustrates a cross-sectional view of the embodiment of FIG. 1 taken along lines 4—4 of FIG. 1.

As shown in FIG. 4, center tube 16 comprises a conduit 20 which has hole 18 therein. Conduit 20 is threaded at exterior end 22, while interior end 24 forms a base which has been molded into dental shield 14 thereby permanently affixing conduit 20 to dental shield 14. Lip shield 12 has a hole therein which allows lip shield 12 to slip over exterior end 22. Nut 26 secures lip shield 12 onto conduit 20. Plastic stop 28 is held by nut 26 and close hole 18 to prevent air from entering the mouth.

Figure 5:
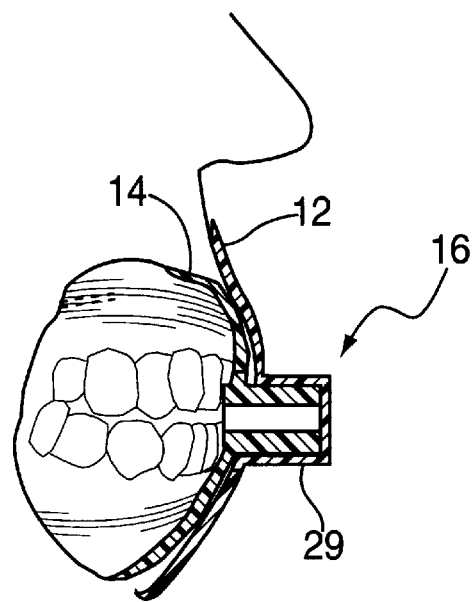
FIG. 5 illustrates the embodiment of FIG. 4 in a users mouth when the mouth is in a rest position.

FIG. 5 illustrates the device of the Invention worn in a users mouth when the mouth is in a rest position. The device of FIG. 5 illustrates nut 26 as blind hole nut 29 which prevents air from entering the users mouth. As can be seen, the users upper and lower lip fit in between lip shield 12 and dental shield 14, while the front of the users teeth abut dental shield 14.

Figure 6:
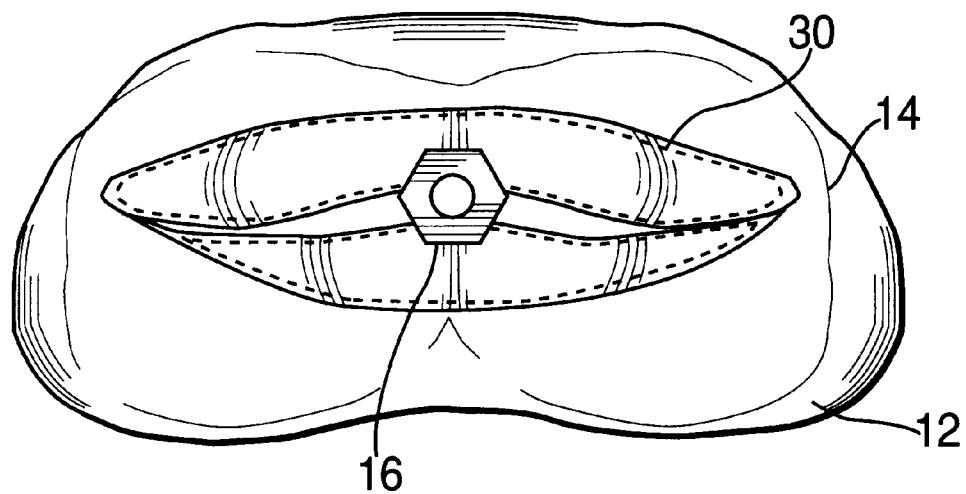
FIG. 6 illustrates a frontal view of the embodiment of FIG. 1 in the users mouth showing the mouth in the rest position.
Figure 7:
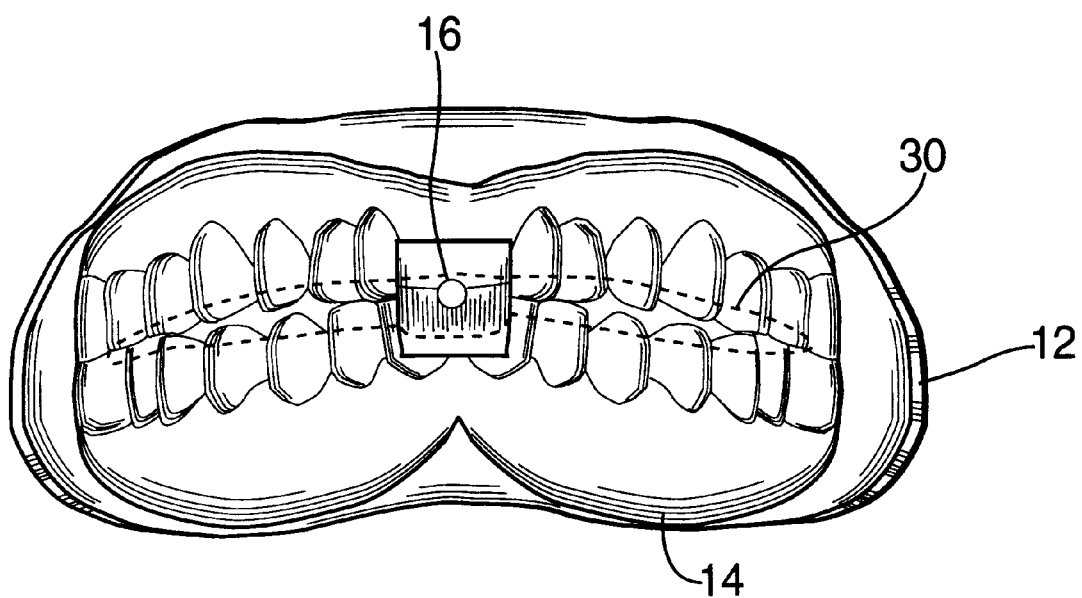
FIG. 7 illustrates a back view of the embodiment of FIG. 1 in the users mouth with the mouth in the rest position.

FIG. 6 illustrates a frontal view of device 10 worn in a users mouth while FIG. 7 illustrates a back view of device 10 worn in a users mouth. As shown therein, lip shield 12 extends vertically over both the upper and lower lips of the user and extends laterally over the full width of the users mouth opening when the mouth is in a rest position. The users lips are shown in dashed lines 30. Dental shield 14 extends vertically over the teeth in both jaws and extends laterally across the teeth in both jaws to the second premolar when the users mouth is in a rest position.

Also, as can be seen by FIGS. 6 and 7, dental shield 14 extends vertically over the back of both the upper and lower lips of the user and extends laterally across the full width of the users mouth opening when the mouth is in the rest position.

Because the lip shield and the dental shield both extend vertically over the lips and extend laterally across the full width of the users mouth opening when the mouth is in the rest position, a substantially airtight seal is formed over the lips and mouth opening preventing mouth breathing and promoting good mouth hygiene.

Figure 8:
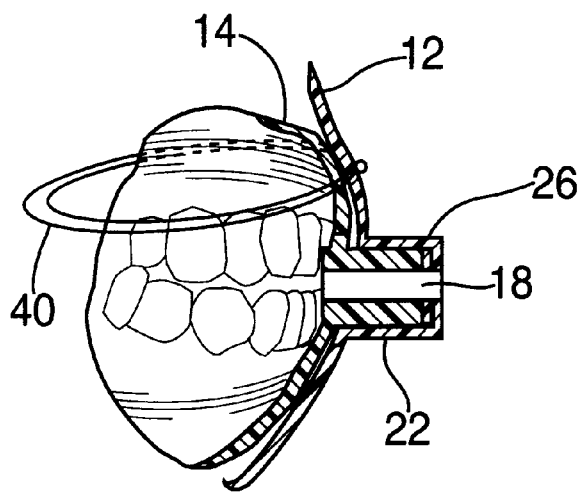
FIG. 8 is a cross-sectional view of another preferred embodiment of the device of the present Invention.

FIG. 8 illustrates another preferred embodiment where nut 26 is an integral part of lip shield 12 while dental shield 14 is integral with conduit 20. Attached to lip shield 12 is head strap 40 which is an elastic band that fits behind the head of the user in order to secure device 10 to the user and hold device 10 in place. Head strap 40 could also be an adjustable strap which attaches to behind the users head by means of a buckle or a Velcro® closure.

Figure 9:
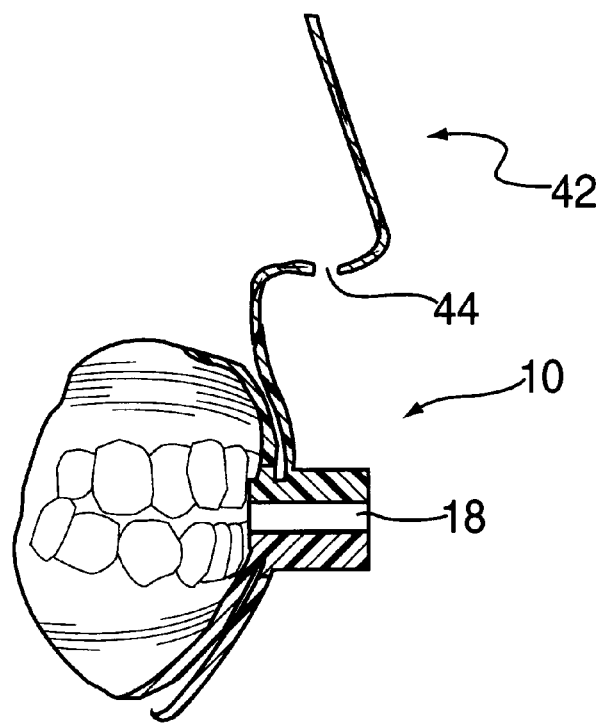
FIG. 9 is a cross-sectional view of yet another preferred embodiment of the device of the present Invention.

FIG. 9 illustrates where lip shield 12, dental shield 14 and center tube 16 as one integral unit. Preferably, the device of the present Invention is configured to allow dental shield 14 to be separated from lip shield 12 for sterilization. Also, as shown in FIG. 9, device 10 has a nose overlay 42 which overlays the users nose and by frictional force helps retain device 10 in a proper position. Nose overlay 42 has holes 44 to allow for breathing through the users nostrils. Nose overlay is preferably molded to conform to the users nose, since nose shapes vary from user to user. Nose overlay 44 is an extension of lip shield 12 as shown in FIG. 9.

Figure 10:
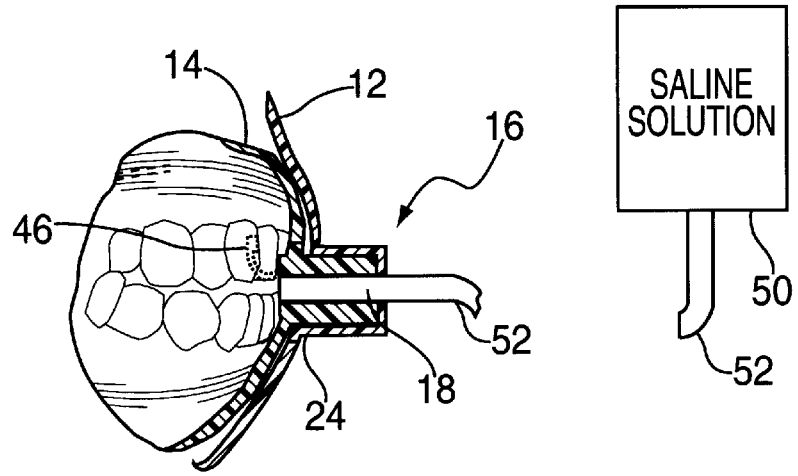
FIG. 10 illustrates the embodiment of FIG. 4 with a saline drip tube.

FIG. 10 illustrates bag 50 connected by tubing 52 which, in turn, is connected to center tube 16. Saline solution or a saliva substitute solution travels through tube 52 and hole 18 and exits at base 24. When the solution exits interior end 24, it flushes the users mouth. Naturally, this assumes that bay 50 is above device 10 and gravity causes the flow of the solution down tube 52 and into the mouth which stimulates the patient to swallow. Also, as shown in FIG. 10, clasp wires 46 are affixed in dental shield 14 and extend from dental shield 14 to hook behind the teeth in the upper jaw and secure device 10 in the users mouth for periods of extended wear. Wires 46 do not effect the closing of the teeth and generally are positioned in embrasures. Such clasp wires are conventional. Bag 50 and tube 52 are a conventional drip tube arrangement which operate in a conventional manner to allow for controlled flow of the solution.

When bag 50 is not connected to center tube 16, hole 18 is closed to prevent the passage of air into the mouth. Hole 18 can be closed in a number of ways. For example, blind hole nut 29 with a blind hole therein such as the one shown in FIG. 5 can be used, or thin plastic piece 28 mounted therein as shown in FIG. 4. Any means can be used to close hole 18, for example, a piece of cellophane held in place by nut 26.

Lip shield 12, dental shield 14 and nose overlay 42 are preferably made of a plastic material which is moldable in a conventional manner to the corresponding parts of a human. Such moldable materials include synthetic rubber, ethyl vinyl acetate, methyl vinyl acetate, methyl acrylate or any thermal plastic material (which can be softer and molded in hot water), other elastic resins which can be softened and molded in hot water and returned to a hardened and stable form upon cooling to room temperature. The preferred material is a synthetic rubber. Such materials are well known to those of skill in the art.

It will be understood that it is intended to cover all changes and modifications of the preferred embodiments herein chosen for the purpose of illustration which do not constitute a departure from the spirit and scope of the invention.

What is claimed is:

1. A mouth breathing preventer for a human being comprising:

a lip shield made of molded plastic material shaped to conform to the curvature of both upper and lower lips, said lip shield extending vertically over both lips and laterally across the complete width of a mouth opening when said mouth is in a rest position;

a dental shield made of molded plastic material shaped to conform to the curvature of both upper and lower teeth, said dental shield extending vertically over teeth in both jaws and laterally across the teeth in both jaws to the second premolar when said mouth is in said rest position; and a center tube connecting said dental shield to said lip shield, said center tube having a hole therein, said center tube adapted to accept a drip tube, and said hole being closable to prevent mouth breathing therethrough.

2. The preventer of claim 1 wherein said center tube is molded into said dental shield and said lip shield is movably affixed to said center tube.

3. The preventer of claim 1 further comprising a means to retain the preventer to the head of the user.

4. The preventer of claim 3 wherein said retainer means is a head strap, a nose overlay or a clasp wire.

* * * * *